(12) United States Patent
Richardson et al.

(10) Patent No.: US 10,471,165 B2
(45) Date of Patent: Nov. 12, 2019

(54) STERILIZATION OR DISINFECTION OF WORKPIECES, INCLUDING MEDICAL AND DENTAL INSTRUMENTS

(71) Applicants: CHEMTREAT, INC., Glen Allen, VA (US); Metrex Research, LLC, Orange, CA (US)

(72) Inventors: John Richardson, Hanover, VA (US); Kevin White, Richmond, VA (US); Benjamin Niemaseck, Chesterfield, VA (US); Douglas McIlwaine, Ashland, VA (US); James Wilkins, Midlothian, VA (US); Rob Bedinger, Richmond, VA (US); Yatao Liu, Cypress, CA (US); James Liang-Hiong Chia, Irvine, CA (US); Stephen C. Fanning, Trabuco Canyon, CA (US); Tim Taylor, Orange, CA (US)

(73) Assignee: CHEMTREAT, INC., Glen Allen, VA (US)

( * ) Notice: Subject to any disclaimer, the term of this patent is extended or adjusted under 35 U.S.C. 154(b) by 103 days.

(21) Appl. No.: 15/688,306

(22) Filed: Aug. 28, 2017

(65) Prior Publication Data

US 2018/0055963 A1    Mar. 1, 2018

Related U.S. Application Data

(60) Provisional application No. 62/379,939, filed on Aug. 26, 2016.

(51) Int. Cl.
*A61L 2/20* (2006.01)

(52) U.S. Cl.
CPC ............ *A61L 2/20* (2013.01); *A61L 2202/14* (2013.01); *A61L 2202/24* (2013.01)

(58) Field of Classification Search
CPC ... A61L 2/20; A61L 2/202; A61L 2/24; A61L 2202/11; A61L 2202/122; A61L 2202/13; A61L 2202/14; A61L 2202/24
See application file for complete search history.

(56) References Cited

U.S. PATENT DOCUMENTS

| 4,504,442 A | 3/1985 | Rosenblatt et al. |
| 4,908,188 A * | 3/1990 | Jefferis, III ............... A61L 2/24 422/110 |

(Continued)

FOREIGN PATENT DOCUMENTS

| GB | 746615 A | 3/1956 |
| WO | 2008/090367 A1 | 7/2008 |
| WO | 2010/019491 A1 | 2/2010 |

OTHER PUBLICATIONS

International Searching Authority, Written Opinion of the International Authority and International Search Report, dated Nov. 7, 2017, 6 pages.

(Continued)

*Primary Examiner* — Timothy C Cleveland
(74) *Attorney, Agent, or Firm* — Oliff PLC

(57) ABSTRACT

Devices and methods for sterilizing and/or disinfecting workpieces, such as medical and dental instruments. The device can include a chamber that receives the workpieces and can be sealed. The chamber is filled with chlorine dioxide gas to a threshold concentration and for a time sufficient to sterilize and/or disinfect the workpieces.

15 Claims, 2 Drawing Sheets

(56) References Cited

U.S. PATENT DOCUMENTS

| | | |
|---|---|---|
| 5,290,524 A | 3/1994 | Rosenblatt et al. |
| 5,476,579 A | 12/1995 | Choi et al. |
| 6,537,821 B1 | 3/2003 | Rosenblatt et al. |
| 6,716,354 B2 | 4/2004 | Rosenblatt et al. |
| 6,824,756 B2 | 11/2004 | Rosenblatt et al. |
| 7,964,138 B2 | 6/2011 | Richardson et al. |
| 8,323,563 B2 | 12/2012 | Richardson et al. |
| 2002/0125196 A1 | 9/2002 | Rosenblatt et al. |
| 2003/0138371 A1 | 7/2003 | McWhorter et al. |
| 2003/0215381 A1 | 11/2003 | Rosenblatt et al. |
| 2004/0258607 A1 | 12/2004 | Rosenblatt et al. |
| 2004/0259188 A1 | 12/2004 | Rosenblatt et al. |
| 2005/0019210 A1 | 1/2005 | Rosenblatt et al. |
| 2007/0178021 A1 | 8/2007 | McWhorter et al. |
| 2007/0183961 A1 | 8/2007 | McWhorter et al. |
| 2008/0139869 A1 | 6/2008 | Wilson et al. |
| 2008/0286147 A1 | 11/2008 | Wilson et al. |
| 2009/0008238 A1 | 1/2009 | Williams |
| 2009/0142226 A1 | 6/2009 | McWhorter et al. |
| 2009/0159538 A1 | 6/2009 | Duve |
| 2010/0025226 A1 | 2/2010 | Callerame |
| 2010/0209528 A1 | 8/2010 | McWhorter et al. |
| 2010/0266448 A1 | 10/2010 | Regits et al. |
| 2012/0131887 A1 | 5/2012 | McWhorter et al. |
| 2012/0135167 A1 | 5/2012 | McWhorter et al. |
| 2012/0148477 A1 | 6/2012 | Rosenblatt et al. |
| 2012/0201898 A1 | 8/2012 | McWhorter et al. |
| 2012/0201899 A1 | 8/2012 | McWhorter et al. |
| 2014/0113007 A1 | 4/2014 | Kato et al. |
| 2016/0206767 A1 | 7/2016 | Park et al. |
| 2016/0251219 A1 | 9/2016 | Richardson et al. |

OTHER PUBLICATIONS

Masschelein, et al. "Chlorine Dioxide—Chemistry and Environmental Impact of Oxychlorine Compounds," Ann Arbor Science, 1979, pp. 35-37.

Apr. 15, 2016 International Search Report issued in International Patent Application No. PCT/US2016/016771.

Apr. 15, 2016 Written Opinion of the International Searching Authority issued in International Patent Application No. PCT/US2016/016771.

Nov. 4 International Preliminary Report on Patentability issued in International Patent Application No. PCT/US16/16771.

* cited by examiner

STERILIZATION OR DISINFECTION OF WORKPIECES, INCLUDING MEDICAL AND DENTAL INSTRUMENTS

CROSS-REFERENCE TO RELATED APPLICATIONS

This application claims the filing date benefit of U.S. Provisional Application No. 62/379,939, filed Aug. 26, 2016, the entirety of which is hereby incorporated herein by reference.

BACKGROUND

For health and safety reasons, there is a need in medical and dental applications to regularly sterilize equipment, particularly before the equipment is next used on a patient or in a procedure. Improperly sterilized instruments utilized in patient care can result in infection, e.g., at a surgical site, and pose a serious threat to the patient's safety that can lead to life-threatening infection or even death. There is also a need in other industries, such as food/beverage and agricultural industries, for regular sterilization of equipment.

In medical and dental applications, controlling infections is an important concern. Equipment contamination by blood or saliva can easily occur. For example, small, sharp instruments can become contaminated with blood or other fluids, providing ample opportunity for transmission of hepatitis B, hepatitis C and human immunodeficiency virus (HIV). Dentistry potentially exposes much of the population to blood contact with infected patients. Thus, the use of dental equipment may pose an unacceptable risk of cross infection.

In dentistry, re-sterilization of used instruments for reuse on another patient has been a common practice. Although, single-use devices have been promoted as a strategy to prevent cross-infection among patients, re-sterilization of previously used instruments still continues to be a common practice because the cost of single-use devices can be significant.

The American Dental Association Guidelines emphasize the importance of dental instrument sterilization, e.g., "All critical and semi critical dental instruments that are heat stable should be sterilized after each use by steam under pressure (autoclaving), dry heat, or chemical vapor . . . . Sterilization is recommended for all high-speed dental handpieces, low-speed handpiece components used intraorally and reusable prophylaxis angles. It is important to follow the manufacturers' instructions for cleaning, lubrication and sterilization procedures to ensure the effectiveness of the sterilization process and the longevity of these instruments. High-speed and low-speed handpieces produced today are heat tolerant, and many older heat sensitive models can be retrofitted with heat-stable components."

The term "disinfection" is understood to be a process that kills only vegetative organisms, whereas, "sterilization" kills spores and other microorganisms as well. Under current practices, sterilizing equipment is a time-consuming process that requires careful attention. If strict protocols are not followed, the equipment may become contaminated. For example, in an autoclave sterilization cycle, interruption of the cycle results in inadequately sterilized instruments that cannot be considered safe. After the sterilization cycle, the sterilizer must depressurize, and the packs remain in the sterilizer for drying. The drying phase may take an additional 20-45 min. The unit must only be opened after completion of the drying cycle making it more time consuming in field settings.

Heat sterilization methods are generally preferred to chemical disinfection. However, with certain instruments that are repeatedly used, frequent chemical disinfection may be necessary since heat sterilization can lead to corrosion. Further, it is often not possible to carry out heat sterilization due to time constraints and the need for access to autoclave equipment.

In these situations, disinfection using chemical disinfectants may be considered an alternate for heat sterilization to reduce the risk of cross contaminations. Glutaraldehyde is a dialdehyde that displays potent bactericidal, fungicidal, mycobactericidal, sporicidal and virucidal activities. The mechanism of its action is based on its interaction with amino groups in proteins and enzymes. Glutaraldehyde is normally used as a 2% solution, which is sufficient to achieve a sporicidal effect. It is used as an immersion solution for metallic instruments, face masks, heat sensitive plastic rubbers, and fiber optics.

Hydrogen peroxide ($H_2O_2$) is also used for disinfection, sterilization, and antisepsis and is effective against bacteria, viruses, yeast and spores. It is commercially available in concentrations ranging from 3% to 90%. $H_2O_2$ is environmental friendly, because it can rapidly degrade into harmless products—water and oxygen. $H_2O_2$ acts as an oxidant by producing hydroxyl free radicals (.OH), which attack cell components, including lipids, proteins, and DNA. A proposed mechanism of action is based on its ability to target exposed sulfhydryl groups and double bonds.

Alcohol is an effective skin antiseptic and disinfectant for medical instruments. A number of alcohols have shown effective antimicrobial activity but, ethyl alcohol, isopropyl alcohol and n-propanol are the most widely used. Alcohols exhibit rapid broad-spectrum antimicrobial activity against vegetative bacteria (including mycobacteria), fungi, and viruses but they lack sporicidal activity hence are not recommended for sterilization. In general, the antimicrobial activity of alcohols is optimum in the range of 60-90%, but it becomes significantly lower at concentrations below 50%. The exact mode of action of alcohols is unclear, but it is generally believed that they cause membrane damage leading to cell lysis and result into a rapid denaturation of proteins.

SUMMARY

Chemical disinfectant technology offers advantages over other methods, such as heat sterilization, but can be less effective. Although a significant reduction in total viable count can be observed with these known chemical disinfectants, it would be desirable to eliminate the viable microorganisms to an even greater degree, and with an easier and more practical method. In summary there is a need for chemical disinfection/sterilization for dental and medical tools, or other workpieces and equipment, e.g., to avoid the spread of infectious diseases.

According to one aspect of this disclosure, there is provided a device for sterilizing or disinfecting a workpiece. The device can include a chamber that defines an interior treatment space, where the chamber can receive the workpiece when the chamber is opened and can be sealed when the chamber is closed. A chlorine dioxide gas source is provided to supply chlorine dioxide gas to the chamber when the chamber is closed. And the device fills the interior treatment space of the chamber with chlorine dioxide gas when the chamber is closed at least until the chlorine dioxide concentration reaches a predetermined threshold concentration.

According to another aspect, there is provided a device for sterilizing or disinfecting a workpiece where the device includes a chamber defining an interior treatment space and the chamber is configured to: (i) be able to receive the workpiece when the chamber is opened, (ii) be sealed when the chamber is closed, and (iii) receive chlorine dioxide gas from a chlorine dioxide gas supply. The device can include a sensor that detects at least one of (i) chlorine dioxide concentration in the interior treatment space, and (ii) pressure in the interior treatment space. The device can further include a controller that is configured to receive information from the sensor and control an amount of chlorine dioxide gas that is supplied to the chamber based on the information that is received from the sensor.

According to another aspect, there is provided a method for treating a workpiece to sterilize or disinfect the workpiece. The method includes steps of introducing the workpiece into a sealable chamber that defines an interior treatment space, sealing the sealable chamber, then filling the interior treatment space with chlorine dioxide gas, and maintaining a concentration of chlorine dioxide in the sealed chamber of at least 1 mg/L for at least two minutes.

DETAILED DESCRIPTION EMBODIMENTS

Aspects of this disclosure relate to the use of chlorine dioxide gas to disinfect or sterilize equipment, tools, medical supplies, fluid lines, dressings and other work pieces. This application describes devices, methods, and systems for these disinfection and sterilization applications.

In one aspect, the chlorine dioxide can be generated as described in U.S. patent application Ser. No. 14/878,603, filed on Oct. 8, 2015 (published as U.S. Patent Application Publication No. 2016/0251219), the entirety of which is incorporated herein by reference. Under this procedure, chlorine dioxide gas can be generated by reacting ozone gas with a solid chlorite media, and the chlorine dioxide that is produced can be used as a disinfectant or sterilizing agent either in gaseous form or dissolved in water. This chlorine dioxide generation method is referred to herein as the "clozone" mechanism.

Figure 1:
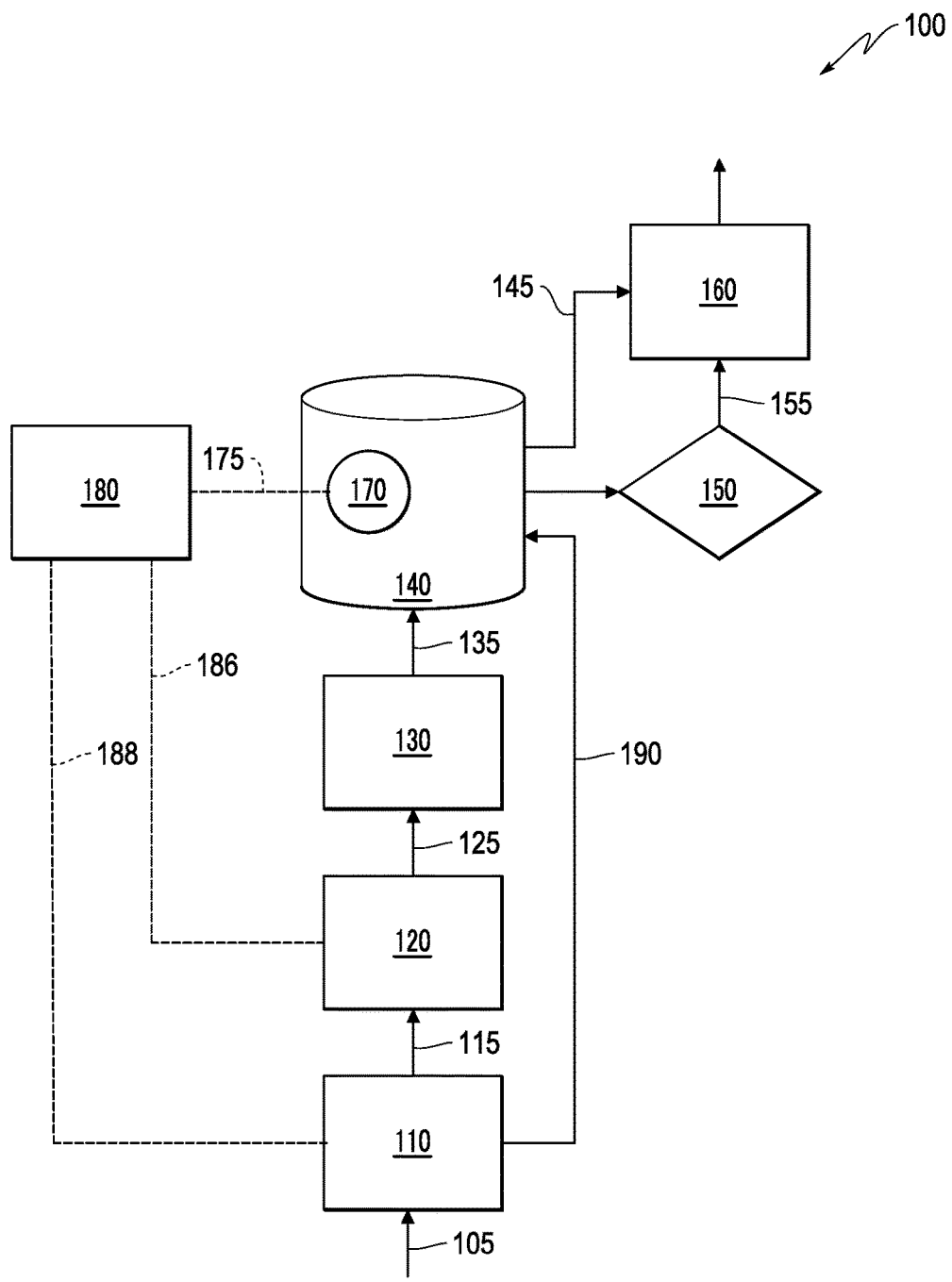
FIG. 1 is a schematic diagram of a sterilization/disinfectant device according to one embodiment of the invention.

FIG. 1 is a schematic diagram that shows a device 100 for sterilization and/or disinfection according to one embodiment of the invention. The device can include an air compressor 110 that receives atmospheric air 105 and generates compressed air 115. The compressed air 115 is delivered to an ozone generator 120 that generates ozone gas 125. As an alternative to the air compressor 110, an oxygen generator may be used that generates purified oxygen that is then supplied to the ozone generator 120. The ozone gas 125 is contacted with solid chlorite media 130 to generate chlorine dioxide gas 135. The solid chlorite media 130 can be provided as chlorite-containing pellets or beads (e.g., containing $Na_2ClO_2$) in a cartridge or column that allows ozone gas to enter the cartridge and allows product gases, including chlorine dioxide, to exit the cartridge. This clozone mechanism can produce very pure chlorine dioxide gas, e.g., higher than 75 wt. % excluding any carrier gas that is included. In some aspects, the invention can include other mechanisms that generate chlorine dioxide gas, particularly those that generate the gas on-site, and on-demand for disinfectant and sterilization.

The device 100 can include probe chamber 140 that can be open and closed. When opened, the chamber 140 is configured to be able to receive workpieces. For example, the chamber 140 may include a lid, door, or clam-shell type structure that is openable and closeable, and preferably can be secured in the closed position with a latch, lock, or interference fit. When closed, the chamber 140 can be sealed to the environment and can define an internal treatment space to which the chlorine dioxide gas 135 is fed to disinfect or sterilize workpieces. The chamber 140 is preferably sealed air-tight from the exterior when it is closed. The interior treatment space of chamber 140 can include sites for holding a single workpiece or multiple workpieces, such as medical and dental equipment. Each holding site can be configured to hold or grip a portion of the workpiece. As one example, the holding sites can be arranged in a row or group, like a rack that is configured to hold multiple instruments.

The chamber 140 can be equipped with one or more sensors 170 including one or more of a chlorine dioxide sensor, a humidity sensor, and a pressure sensor. The chamber 140 can further include a sensor that senses when the chamber is open to the outside environment or closed, and a sensor that can sense whether there is a workpiece being held in the chamber (e.g., with a weight sensor, contact sensor, capacitance sensor, or the like). The sensors can be connected to communicate with a control system 180 (e.g., by being hard-wired or wirelessly connected over communication pathway 175).

Figure 2:
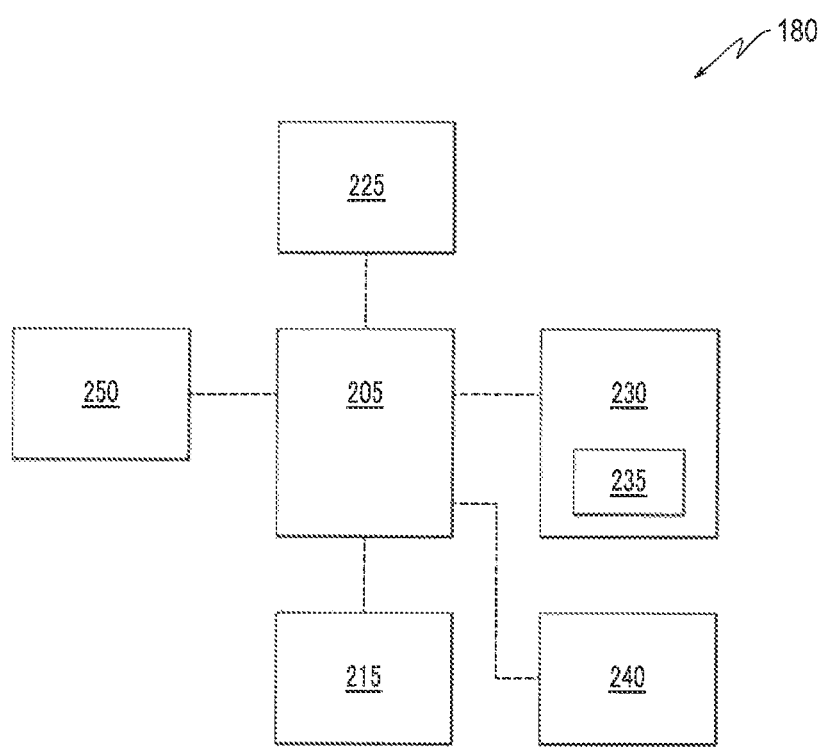
FIG. 2 is a schematic diagram of a control system that can be used with the sterilization/disinfectant device.

The control system 180 is illustrated schematically in FIG. 2. The control system 180 can include a controller such as processor (e.g., CPU 205), a memory 215 such as a hard drive or flash drive, which may include ROM memory, and a timer 225. The timer 225 can include a quartz clock, for example. The CPU 205 can communicate with a display 230. The device 100 can include a user interface 235 as part of the display 230 or as a separate interface, e.g., on the chamber 140. The CPU can also communicate with a light display 240 that includes various lights (e.g., LED) to visually indicate the status of treatment, e.g., a specific light, color, or other indicia can indicate on-going treatment, time to end of treatment, completion of treatment period, storage, not treated, etc.). The light display 240 can be positioned on the probe chamber 140, for example.

To disinfect or sterilize a workpiece, the control system 180 can activate chlorine dioxide gas generation, e.g., by sending "ON" signals to the air compressor 110 and the ozone generator 120 via respective communication pathways 188 and 186. The chlorine dioxide gas generation can be controlled to fill the sealed chamber 140 with chlorine dioxide gas until the chlorine dioxide level in the chamber 140 reaches a predetermined threshold concentration, e.g., at least 1 mg/L to 2,000 mg/L, at least 5 mg/L to 1,000 mg/L, at least 10 mg/L to 500 mg/L, at least 25 mg/L to 250 mg/L, or at least 50 mg/L to 200 mg/L.

The control system 180 can continue to control the concentration of chlorine dioxide in the chamber based on information from sensor 170, such as chlorine dioxide sensor, so that the chlorine dioxide gas can be maintained in the chamber at a minimum threshold concentration. For example, where a clozone reaction mechanism is employed, the control system 180 can control the amount of ozone produced by the ozone generator 120 by changing the voltage to the ozone generator 120 by sending signals via communication pathway 186, and by controlling the amount of oxygen fed to the generator 120, e.g., by controlling the output of the air compressor 110 via communication pathway 188.

Increasing the amount of ozone will increase the amount of chlorine dioxide gas that is generated, which allows the chlorine dioxide concentration in the chamber 140 to be quickly controlled. This control can be performed automatically by the control system 180 using a control loop feedback mechanism, such as a PID controller. Aspects of this invention may allow the target concentration in the chamber to be reached in a manner of minutes, e.g., depending on the chamber volume, from 10 seconds to 45 minutes, from 30 seconds to 30 minutes or from 1 to 15 minutes.

The pressure in the chamber can also be controlled automatically in a similar manner by using a pressure sensor that communicates with the control system 180 so that the chlorine dioxide generation is controlled to achieve the desired pressure. In this way, the chlorine dioxide concentration in chamber 140 could also be controlled by using only information from the pressure sensor.

In one aspect, the pressure can also be controlled with a pressure relief valve 150 that allows pressure in the chamber to build up to a desired threshold pressure when the chamber is filled with chlorine dioxide gas, and which releases gas 155 in any amount necessary to maintain the threshold pressure. When filled with chlorine dioxide gas, the pressure in the chamber 140 can be kept at atmospheric pressure, or desirably slightly above atmospheric pressure, e.g., at least 1 psi, 5 psi, or 1-10 psi over atmospheric pressure, Maintaining a slight back pressure in the chamber 140 in this manner can increase the effectiveness of the chlorine dioxide in sterilizing or disinfecting the workpiece because, e.g., it can force the gas into crevices and cracks of the workpiece and ensures that the entire chamber is filled with chlorine dioxide gas at the desired concentration.

The pressure relief valve 150 can be connected to a gas scrubber 160 that adsorbs or neutralizes the chlorine dioxide in gas 155. The scrubber 160 can be a container that includes activated carbon, for example. The scrubber 160 can likewise be connected to an evacuation line 145 to evacuate the chlorine dioxide gas from the chamber 140 before opening the chamber so that the sterilized or disinfected workpieces can be safely removed.

The humidity in the chamber can be separately controlled based on information from the humidity sensor. It may be desirable in some circumstances to maintain a somewhat humid environment in the chamber when treating the workpiece to sterilize or disinfect it. In this regard, the humidity may condense on hard surfaces of the workpiece and act as a vehicle in which the chlorine dioxide dissolves in the condensate and disinfects the surface.

The control system 180 can include a timer 225 that can keep track of the sterilization or disinfecting time, i.e., the time that has elapsed since the chlorine dioxide reached the target concentration and/or pressure. The CPU 205 can send signals causing an audio alert or visual alert (e.g., on the user interface 235 or light display 240 on the device) when the desired sterilization or disinfecting treatment period is complete. Suitable periods will depend on the application and the desired level of sterilization, but may be in the range of from 2 minutes to three hours, from 10 minutes to two hours, or from 30 minutes to one hour, for example.

In some embodiments, the chamber 140 can be used for storing workpieces in the presence of chlorine dioxide gas until they are needed for use. During such storage, the concentration and/or pressure of chlorine dioxide in the chamber can be maintained at the same or different values as that used during the sterilization/disinfection step. For example, the CPU 205 can automatically terminate the sterilization/disinfection step after a threshold time has elapsed, and control the chlorine dioxide generation and/or air compressor output to change the environment from a treatment concentration/pressure to a storage concentration/pressure. The storage concentration of chlorine dioxide may be less than the treatment concentration of chlorine dioxide.

In this regard, air 190 can be supplied directly from the air compressor 110 to chamber 140 (separately from the ozone generator) to reduce the concentration of chlorine dioxide in the chamber 140 after the sterilization disinfecting step, to evacuate the chamber, or reduce the concentration to a suitable storage concentration. The user interface can include an input for instructing the chamber 140 to evacuate the trapped chlorine dioxide gas via line 145 so that a workpiece can be safely removed.

If the chamber 140 includes sites for holding more than one workpiece, the chamber 140 can include a plurality of chambers or the chamber 140 can be divided into one or more discrete subchambers, where chlorine dioxide is fed to each chamber separately from the chlorine dioxide generation unit, e.g., through a manifold that has a line and valve to each subchamber, and where the valves are connected to the control system. Under such a configuration, one chamber can hold a workpiece in an environment with a storage concentration of chlorine dioxide while another chamber is treating a second workpiece in an environment with a treatment concentration of chlorine dioxide.

The ability to store a workpiece in a chlorine dioxide-containing atmosphere is advantageous because the user has confidence that the workpiece is sterile (or disinfected) when the user removes it from the chamber for use. In this regard, in known disinfectant systems, the workpiece is removed upon completion of treatment and may be stored in conditions that compromise the disinfectant treatment Until it is later used. This can be particularly problematic with liquid media disinfection solutions because liquid can remain on the workpiece after being removed from the device, which can promote microbial growth. Also, by storing the workpiece in a chlorine dioxide-containing atmosphere, the storage period can be relatively lengthy while maintaining an atmosphere that prevents microbe growth. In some aspects, the storage period may be at least up to one week, up to three days, or from 2 hours to 1 day.

The sterilization/disinfection device described herein can further be provided with a mechanism to track and record information about the disinfection/sterilization of a specific workpiece. For example, the device 100 can include a laser scanner 250 that scans a barcode on a workpiece and then records in the memory 215 (i) whether that specific workpiece has been treated, (ii) for how long, (iii) the treatment conditions (chlorine dioxide concentration and pressure), (iv) the storage time and conditions, (v) etc. Equivalent tracking systems such as employing REID chip on the workpiece and a reader on the sterilization/disinfectant device can also be used. The information that is specific to status of the workpiece can be recorded in memory 215 and retrieved by the user at the user interface 235 or on separate display so that the user has confidence that the workpiece is suitable for use.

In one aspect, the invention allows many of the above steps to be automated. For example, the device 100 may detect when a workpiece has been inserted into the chamber 140, and automatically begin a treatment cycle, and when the treatment cycle is complete it can automatically begin a storage cycle. The conditions in the chamber 140 can also be automatically controlled using control feedback mechanisms, as described above.

Using a gaseous disinfectant medium that can be generated on-site and can be provided on-demand has several advantages:

The use of a gaseous medium, particularly gas that is generated on-site, allows for any sized chamber to be used in connection with the invention. In this regard, even large chambers can be readily filled to the desired concentration, which allows for large workpieces to be disinfected or allows a large number of workpieces to be simultaneously disinfected. Suitable treatment chambers may have a volume in the range of, for example, from 10 ml to 50 L, from 100 ml to 10 L, from 500 ml to 5 L, or from 750 ml to 3 L.

The chlorine dioxide can be quickly generated (e.g., at a rate of at least 0.5 g/hour, at least 1 g/hr, at least 10 g/hr, or 5-20 g/hr), and the chamber can be quickly filled at a precise pressure and concentration. The concentration and pressure can be determined empirically, for example, based on the levels that show required efficacy against certain microbes of interest for a given application or for the type of equipment that is being disinfected. The memory 215 can store a database of concentrations and/or pressures of chlorine dioxide that are effective against specific microbes (i.e., the values that show microbe concentrations at less than a predetermined threshold value for a given treatment time), and the control system 180 can be configured to retrieve this recorded information and control the chamber to achieve these conditions based on input from a user regarding, e.g., the level of disinfection/sterilization that is needed.

The chlorine dioxide generation unit can be a sustainable portable unit that comprises, in the clozone method, the air compressor 110, the ozone generator 120, and the chlorite media 130. The portable unit can be linked to a host system including, e.g., the probe chamber 140, control system 180, etc. to provide onsite antimicrobial/biocide gas. The chlorite media can be provided in a cartridge that is replaceable as the media is depleted.

The chlorine dioxide allows for sterilization/disinfection at low temperatures (typically less than 35° C., less than 30° C., from 20-25° C., or room temperature), and thus allows for treatment of workpieces that cannot be sterilized at higher temperatures, such as in an autoclave. This may include workpieces with polymeric parts, thin films, nonwoven materials, fibrous materials, etc.

Using a tracking system as described above can provide a foolproof mechanism for ensuring that workpieces are sterilized or disinfected to the desired level. Current systems are manual, and chemical indicators are required to show that treatment is complete. By using a gaseous disinfectant media with tracking and the ability to store the treated workpiece, less human interaction is required as compared to liquid media. For example, using chlorine dioxide gas prevents the need to rinse the workpiece, which is required when liquid chemicals are used. The storage and tracking system described above also provide an automated system, not practical with liquid media, that reduces errors.

This disclosure has been presented for purposes of illustration and description and is not intended to be exhaustive or limiting. Modifications and variations will be apparent to those of ordinary skill in the art, while still practicing the inventions defined in the claims. The embodiments were chosen and described in order to explain principles and practical applications, and to enable others of ordinary skill in the art to understand the disclosure for various embodiments with various modifications as are suited to the particular use contemplated.

What is claimed is:

1. A device for sterilizing or disinfecting a workpiece, the device comprising:
    a chamber defining an interior treatment space, the chamber being configured to be able to receive the workpiece when the chamber is opened and to be sealed when the chamber is closed;
    a chlorine dioxide gas source that is configured to supply chlorine dioxide gas to the chamber when the chamber is closed, the chlorine dioxide gas source being further configured to generate the chlorine dioxide gas by contacting a dry chlorite reactant media with an ozone-containing gas,
    wherein the device is configured to fill the interior treatment space with the chlorine dioxide gas when the chamber is closed at least until the chlorine dioxide concentration in the internal treatment space reaches a predetermined threshold concentration.

2. The device according to claim 1, further comprising a chlorine dioxide sensor that is configured to detect chlorine dioxide concentration in the interior treatment space.

3. The device according to claim 2, further comprising a controller that is configured to receive information from the chlorine dioxide sensor, and is configured to send signals to control an amount of the chlorine dioxide gas that the chlorine dioxide gas source supplies to the chamber based on the information received from the chlorine dioxide sensor.

4. The device according to claim 1, further comprising an ozone generator that is configured to generate the ozone-containing gas, and wherein the ozone-containing gas is supplied to the dry chlorite reactant media.

5. The device according to claim 4, further comprising an air compressor that supplies compressed air to the ozone generator.

6. The device according to claim 5, further comprising a controller that is configured to send signals to at least one of the ozone generator and air compressor to control the amount of chlorine dioxide gas that is supplied to the chamber.

7. The device according to claim 1, further comprising a pressure sensor that is configured to detect pressure in the interior treatment space.

8. The device according to claim 1, wherein the device is configured to be able to control the humidity in the interior treatment space.

9. The device according to claim 1, further comprising a scrubber that is configured to receive evacuated gas from the chamber, and wherein the scrubber is further configured to adsorb or neutralize chlorine dioxide in the evacuated gas.

10. The device according to claim 1, further comprising a pressure relief valve that releases gas in the chamber if the chamber exceeds a threshold pressure.

11. The device according to claim 1, wherein the interior treatment space of the chamber includes a plurality of holding sites that are configured to hold medical and/or dental instruments.

12. The device according to claim 1, wherein the device is configured to fill the interior treatment space with the chlorine dioxide gas so that the concentration of chlorine dioxide in the interior treatment space is in the range of from 5 mg/L to 1,000 mg/L.

13. The device according to claim 1, wherein the device is configured to maintain the concentration of chlorine dioxide in the internal treatment space at or above the predetermined threshold concentration for a treatment period of from 2 minutes to three hours.

14. The device according to claim 13, wherein, after the treatment period, the device is configured to change the concentration of chlorine dioxide in the chamber to a second predetermined threshold concentration for storing the workpiece while the chamber remains in the closed position.

15. The device according to claim 1, wherein the chlorine dioxide gas source is configured so that ozone in the ozone-containing gas reacts with chlorite in the dry chlorite reactant media at a gas-solid interface between the ozone-containing gas and the dry chlorite reactant media to produce the chlorine dioxide gas.

* * * * *